US007780662B2

(12) United States Patent
Bahney (10) Patent No.: US 7,780,662 B2
(45) Date of Patent: Aug. 24, 2010

(54) VESSEL SEALING SYSTEM USING CAPACITIVE RF DIELECTRIC HEATING

(75) Inventor: Timothy J. Bahney, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 882 days.

(21) Appl. No.: 11/063,684

(22) Filed: Feb. 23, 2005

(65) Prior Publication Data

US 2005/0197659 A1 Sep. 8, 2005

Related U.S. Application Data

(60) Provisional application No. 60/549,232, filed on Mar. 2, 2004.

(51) Int. Cl.
*A61B 18/14* (2006.01)
(52) U.S. Cl. ...................................... 606/51
(58) Field of Classification Search ............... 606/50–52
See application file for complete search history.

(56) References Cited

U.S. PATENT DOCUMENTS

| 1,787,709 | A | 1/1931 | Wappler |
| 1,813,902 | A | 7/1931 | Bovie |
| 1,841,968 | A | 1/1932 | Lowry |
| 1,863,118 | A | 6/1932 | Liebel |
| 1,945,867 | A | 2/1934 | Rawls |
| 2,827,056 | A | 3/1958 | Degelman |
| 2,849,611 | A | 8/1958 | Adams |
| 2,982,881 | A | 5/1961 | Reich |
| 3,058,470 | A | 10/1962 | Seeliger et al. |
| 3,089,496 | A | 5/1963 | Degelman |
| 3,163,165 | A | 12/1964 | Islikawa |
| 3,252,052 | A | 5/1966 | Nash |
| 3,391,351 | A | 7/1968 | Trent |
| 3,402,326 | A | 9/1968 | Guasco et al. |
| 3,413,480 | A | 11/1968 | Biard et al. |
| 3,436,563 | A | 4/1969 | Regitz |
| 3,439,253 | A | 4/1969 | Piteo |

(Continued)

FOREIGN PATENT DOCUMENTS

DE 179607 3/1905

(Continued)

OTHER PUBLICATIONS

Medtrex Brochure "The O.R. Pro 300" 1 p. Sep. 1998.

(Continued)

*Primary Examiner*—Lee S Cohen (57) ABSTRACT

An electrosurgical system for sealing vessels using capacitive (RF) dielectric heating and a method thereof are provided. The system includes an electrosurgical instrument having an end effector with parallel plate electrodes that will clamp onto a vessel and maintain a specified gap distance; however, the electrodes will be coated with a non-conductive dielectric material. Such an end effector will ensure that direct conduction between the electrodes does not occur through tissue or fluids and effectively creates a parallel plate capacitor with a dielectric, e.g., tissue and coating, in between the plates. The electrosurgical instrument will be activated with an AC signal at a specified RF frequency, e.g., a Debye resonance frequency, via an electrosurgical generator. An effective AC current will flow through the tissue and cause heating due to fictional losses from rotating polar molecules in the tissue.

13 Claims, 7 Drawing Sheets

U.S. PATENT DOCUMENTS

| | | |
|---|---|---|
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,482 A | 10/1973 | Shaw |
| 3,783,340 A | 1/1974 | Becker |
| 3,784,842 A | 1/1974 | Kremer |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,828,768 A | 8/1974 | Douglas |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,901,216 A | 8/1975 | Felger |
| 3,905,373 A | 9/1975 | Gonser |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,980,085 A | 9/1976 | Ikuno |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,063,557 A | 12/1977 | Wuchinich et al. |
| 4,074,719 A | 2/1978 | Semm |
| 4,092,986 A | 6/1978 | Schneiderman |
| 4,094,320 A | 6/1978 | Newton et al. |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,145,636 A | 3/1979 | Doi |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,209,018 A | 6/1980 | Meinke et al. |
| 4,231,372 A | 11/1980 | Newton |
| 4,232,676 A | 11/1980 | Herczog |
| 4,237,887 A | 12/1980 | Gosner |
| 4,237,891 A | 12/1980 | DuBose et al. |
| 4,281,373 A | 7/1981 | Mabille |
| 4,287,557 A | 9/1981 | Brehse |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,364,390 A | 12/1982 | Shaw |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,407,272 A | 10/1983 | Yamaguchi |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,452,546 A | 6/1984 | Hiltebrandt et al. |
| 4,463,759 A | 8/1984 | Garito et al. |
| 4,470,414 A | 9/1984 | Imagawa et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,576,177 A | 3/1986 | Webster, Jr. |
| 4,582,057 A | 4/1986 | Auth et al. |
| 4,590,934 A | 5/1986 | Malis et al. |
| 4,608,977 A | 9/1986 | Brown |
| 4,630,218 A | 12/1986 | Hurley |
| 4,632,109 A | 12/1986 | Patterson |
| 4,644,955 A | 2/1987 | Mioduski |
| 4,646,222 A | 2/1987 | Okado et al. |
| 4,651,264 A | 3/1987 | Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,712,559 A | 12/1987 | Turner |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,754,757 A | 7/1988 | Feucht |
| 4,788,634 A | 11/1988 | Schlecht et al. |
| 4,805,621 A | 2/1989 | Heinze et al. |
| 4,818,954 A | 4/1989 | Flachenecker et al. |
| 4,827,911 A | 5/1989 | Broadwin et al. |
| 4,827,927 A | 5/1989 | Newton |
| 4,832,024 A | 5/1989 | Boussignac et al. |
| 4,848,335 A | 7/1989 | Manes |
| 4,848,355 A | 7/1989 | Nakamura et al. |
| 4,860,745 A | 8/1989 | Farin et al. |

| Patent No. | Date | Inventor |
|---|---|---|
| 4,862,889 A | 9/1989 | Feucht |
| 4,880,719 A | 11/1989 | Murofushi et al. |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,961,047 A | 10/1990 | Carder |
| 4,961,435 A | 10/1990 | Kitagawa et al. |
| 4,966,597 A | 10/1990 | Cosman |
| RE33,420 E | 11/1990 | Sussman |
| 4,969,885 A | 11/1990 | Farin |
| 4,993,430 A | 2/1991 | Shimoyama et al. |
| 4,995,877 A | 2/1991 | Ams et al. |
| 5,015,227 A | 5/1991 | Broadwin et al. |
| 5,019,176 A | 5/1991 | Brandhorst, Jr. |
| 5,024,668 A | 6/1991 | Peters et al. |
| 5,029,588 A | 7/1991 | Yock et al. |
| 5,087,257 A | 2/1992 | Farin |
| 5,103,804 A | 4/1992 | Abele et al. |
| 5,108,389 A | 4/1992 | Cosmescu |
| 5,108,391 A | 4/1992 | Flachenecker |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,162,217 A | 11/1992 | Hartman |
| 5,167,658 A | 12/1992 | Ensslin |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,249,121 A | 9/1993 | Baum et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin |
| 5,281,213 A | 1/1994 | Milder et al. |
| 5,300,068 A | 4/1994 | Rosar et al. |
| 5,300,070 A | 4/1994 | Gentelia |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,193 A | 8/1994 | Nardella |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,348,554 A | 9/1994 | Imran et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,396,062 A | 3/1995 | Eisentraut et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,006 A | 4/1995 | Buchholtz et al. |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,423,808 A | 6/1995 | Edwards et al. |
| 5,423,809 A | 6/1995 | Klicek |
| 5,423,810 A | 6/1995 | Goble et al. |
| 5,425,704 A | 6/1995 | Sakurai et al. |
| 5,430,434 A | 7/1995 | Lederer et al. |
| 5,432,459 A | 7/1995 | Thompson |
| 5,433,739 A | 7/1995 | Sluijter et al. |
| 5,434,398 A | 7/1995 | Goldberg |
| 5,436,566 A | 7/1995 | Thompson |
| 5,438,302 A | 8/1995 | Goble |
| 5,443,463 A | 8/1995 | Stern et al. |
| 5,445,635 A | 8/1995 | Denen |
| 5,451,224 A | 9/1995 | Goble et al. |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,478,303 A | 12/1995 | Folry-Nolan et al. |
| 5,480,399 A | 1/1996 | Hebborn |
| 5,483,952 A | 1/1996 | Aranyi |
| 5,490,850 A | 2/1996 | Ellman et al. |
| 5,496,312 A | 3/1996 | Klicek |
| 5,496,313 A | 3/1996 | Gentelia et al. |
| 5,500,012 A | 3/1996 | Brucker et al. |
| 5,500,616 A | 3/1996 | Ochi |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,681 A | 7/1996 | Strul et al. |
| 5,540,683 A | 7/1996 | Ichikawa |
| 5,540,684 A | 7/1996 | Hassler, Jr. |
| 5,540,724 A | 7/1996 | Cox |
| 5,556,396 A | 9/1996 | Cohen et al. |
| 5,558,671 A | 9/1996 | Yates |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,594,636 A | 1/1997 | Schauder |
| 5,596,466 A | 1/1997 | Ochi |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,613,966 A | 3/1997 | Makower et al. |
| 5,613,996 A | 3/1997 | Lindsay |
| 5,625,370 A | 4/1997 | D'Hont |
| 5,626,575 A | 5/1997 | Crenner |
| 5,628,745 A | 5/1997 | Bek |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,674,217 A | 10/1997 | Wahlstrom et al. |
| 5,685,840 A | 11/1997 | Schechter et al. |
| 5,688,267 A | 11/1997 | Panescu et al. |
| 5,690,692 A | 11/1997 | Fleming |
| 5,693,042 A | 12/1997 | Bioarski et al. |
| 5,694,304 A | 12/1997 | Telefus et al. |
| 5,695,494 A | 12/1997 | Becker |
| 5,696,351 A | 12/1997 | Benn et al. |
| 5,702,386 A | 12/1997 | Stern et al. |
| 5,702,429 A | 12/1997 | King |
| 5,707,369 A | 1/1998 | Vaitekunas et al. |

| | | | | | | |
|---|---|---|---|---|---|---|
| 5,712,772 | A | 1/1998 | Telefus et al. | 6,210,403 B1 | 4/2001 | Klicek |
| 5,713,896 | A | 2/1998 | Nardella | 6,228,080 B1 | 5/2001 | Gines |
| 5,720,744 | A | 2/1998 | Eggleston et al. | 6,228,081 B1 | 5/2001 | Goble |
| 5,722,975 | A | 3/1998 | Edwards et al. | 6,231,569 B1 | 5/2001 | Bek |
| 5,733,281 | A | 3/1998 | Nardella | 6,235,020 B1 | 5/2001 | Cheng et al. |
| 5,749,869 | A | 5/1998 | Lindenmeier et al. | 6,238,387 B1 | 5/2001 | Miller, III |
| 5,749,871 | A | 5/1998 | Hood et al. | 6,238,388 B1 | 5/2001 | Ellman |
| 5,755,715 | A | 5/1998 | Stern | 6,241,725 B1 | 6/2001 | Cosman |
| 5,766,165 | A | 6/1998 | Gentelia et al. | 6,245,065 B1 | 6/2001 | Panescu |
| 5,769,847 | A | 6/1998 | Panescu | 6,246,912 B1 | 6/2001 | Sluijter et al. |
| 5,772,659 | A | 6/1998 | Becker et al. | 6,251,106 B1 | 6/2001 | Becker et al. |
| 5,792,138 | A | 8/1998 | Shipp | 6,258,085 B1 | 7/2001 | Eggleston |
| 5,797,802 | A | 8/1998 | Nowak | 6,261,285 B1 | 7/2001 | Novak |
| 5,797,902 | A | 8/1998 | Netherly | 6,261,286 B1 | 7/2001 | Goble et al. |
| 5,814,092 | A | 9/1998 | King | 6,273,886 B1 | 8/2001 | Edwards |
| 5,817,093 | A | 10/1998 | Williamson, IV et al. | 6,275,786 B1 | 8/2001 | Daners |
| 5,820,568 | A | 10/1998 | Willis | 6,293,941 B1 | 9/2001 | Strul |
| 5,827,271 | A | 10/1998 | Bussey et al. | 6,293,942 B1 | 9/2001 | Goble et al. |
| 5,830,212 | A | 11/1998 | Cartmell | 6,296,636 B1 | 10/2001 | Cheng et al. |
| 5,836,909 | A | 11/1998 | Cosmescu | 6,303,166 B1 | 10/2001 | Kolbe et al. |
| 5,836,943 | A | 11/1998 | Miller, III | 6,306,131 B1 | 10/2001 | Hareyama et al. |
| 5,836,990 | A | 11/1998 | Li | 6,306,134 B1 | 10/2001 | Goble et al. |
| 5,846,236 | A | 12/1998 | Lindenmeier et al. | 6,309,386 B1 | 10/2001 | Bek |
| 5,868,737 | A | 2/1999 | Taylor et al. | 6,325,799 B1 | 12/2001 | Goble |
| 5,868,739 | A | 2/1999 | Lindenmeier et al. | 6,337,998 B1 | 1/2002 | Behl et al. |
| 5,868,740 | A | 2/1999 | LeVeen et al. | 6,338,657 B1 | 1/2002 | Harper et al. |
| 5,871,481 | A | 2/1999 | Kannenberg et al. | 6,350,262 B1 | 2/2002 | Ashley |
| 5,891,142 | A * | 4/1999 | Eggers et al. ............... 606/51 | 6,358,245 B1 | 3/2002 | Edwards |
| 5,897,552 | A | 4/1999 | Edwards et al. | 6,364,877 B1 | 4/2002 | Goble et al. |
| 5,908,444 | A | 6/1999 | Azure | 6,383,183 B1 | 5/2002 | Sekino et al. |
| 5,913,882 | A | 6/1999 | King | 6,391,024 B1 | 5/2002 | Sun et al. |
| 5,921,982 | A | 7/1999 | Lesh et al. | 6,398,779 B1 | 6/2002 | Buysse et al. |
| 5,925,070 | A | 7/1999 | King et al. | 6,398,781 B1 | 6/2002 | Goble et al. |
| 5,931,836 | A | 8/1999 | Hatta et al. | 6,402,741 B1 | 6/2002 | Keppel et al. |
| 5,938,690 | A | 8/1999 | Law et al. | 6,402,743 B1 | 6/2002 | Orszulak et al. |
| 5,948,007 | A | 9/1999 | Starkebaum et al. | 6,416,509 B1 | 7/2002 | Goble et al. |
| 5,951,545 | A | 9/1999 | Schilling | 6,436,096 B1 | 8/2002 | Hareyama |
| 5,951,546 | A | 9/1999 | Lorentzen | 6,451,015 B1 | 9/2002 | Rittman, III et al. |
| 5,954,686 | A | 9/1999 | Garito et al. | 6,458,121 B1 | 10/2002 | Rosenstock |
| 5,954,717 | A | 9/1999 | Behl et al. | 6,464,689 B1 | 10/2002 | Qin |
| 5,954,719 | A | 9/1999 | Chen et al. | 6,464,696 B1 | 10/2002 | Oyama |
| 5,961,344 | A | 10/1999 | Rosales et al. | 6,506,189 B1 | 1/2003 | Rittman, III et al. |
| 5,971,980 | A | 10/1999 | Sherman | 6,508,815 B1 | 1/2003 | Strul |
| 5,976,128 | A | 11/1999 | Schilling et al. | 6,511,476 B2 | 1/2003 | Hareyama |
| 5,983,141 | A | 11/1999 | Sluijter et al. | 6,511,478 B1 | 1/2003 | Burnside et al. |
| 6,010,499 | A | 1/2000 | Cobb | 6,517,538 B1 | 2/2003 | Jacob et al. |
| 6,014,581 | A | 1/2000 | Whayne et al. | 6,524,308 B1 | 2/2003 | Muller et al. |
| 6,033,399 | A | 3/2000 | Gines | 6,547,786 B1 | 4/2003 | Goble |
| 6,044,283 | A | 3/2000 | Fein et al. | 6,558,376 B2 | 5/2003 | Bishop |
| 6,053,910 | A | 4/2000 | Fleenor | 6,562,037 B2 | 5/2003 | Paton |
| 6,053,912 | A | 4/2000 | Panescu et al. | 6,565,559 B2 | 5/2003 | Eggleston |
| 6,055,458 | A | 4/2000 | Cochran et al. | 6,573,248 B2 | 6/2003 | Ramasamy et al. |
| 6,056,745 | A | 5/2000 | Panescu et al. | 6,575,969 B1 | 6/2003 | Rittman, III et al. |
| 6,056,746 | A | 5/2000 | Goble et al. | 6,582,427 B1 | 6/2003 | Goble et al. |
| 6,063,075 | A | 5/2000 | Mihori | 6,602,252 B2 * | 8/2003 | Mollenauer ............... 606/46 |
| 6,063,078 | A | 5/2000 | Wittkampf | 6,620,157 B1 | 9/2003 | Dabney et al. |
| 6,066,137 | A * | 5/2000 | Greep ............... 606/45 | 6,623,423 B2 | 9/2003 | Sakurai et al. |
| 6,068,627 | A | 5/2000 | Orszulak et al. | 6,626,901 B1 * | 9/2003 | Treat et al. ............... 606/29 |
| 6,074,386 | A | 6/2000 | Goble et al. | 6,635,057 B2 | 10/2003 | Harano |
| 6,074,388 | A | 6/2000 | Tockweiler et al. | 6,648,883 B2 | 11/2003 | Francischelli |
| 6,080,149 | A | 6/2000 | Huang et al. | 6,652,514 B2 | 11/2003 | Ellman |
| 6,093,186 | A | 7/2000 | Goble | 6,656,177 B2 * | 12/2003 | Truckai et al. ............... 606/51 |
| 6,102,497 | A | 8/2000 | Ehr et al. | 6,663,623 B1 | 12/2003 | Oyama et al. |
| RE36,871 | E | 9/2000 | Epstein | 6,663,624 B2 | 12/2003 | Edwards |
| 6,113,591 | A | 9/2000 | Whayne et al. | 6,666,860 B1 | 12/2003 | Takahashi |
| 6,113,596 | A | 9/2000 | Hooven | 6,679,875 B2 | 1/2004 | Honda |
| 6,123,702 | A | 9/2000 | Swanson et al. | 6,682,527 B2 | 1/2004 | Strul |
| 6,132,429 | A | 10/2000 | Baker | 6,685,700 B2 | 2/2004 | Behl |
| 6,142,992 | A | 11/2000 | Cheng et al. | 6,685,701 B2 | 2/2004 | Orszulak et al. |
| 6,155,975 | A | 12/2000 | Urich et al. | 6,692,489 B1 | 2/2004 | Heim |
| 6,162,217 | A | 12/2000 | Kannenberg et al. | 6,712,813 B2 | 3/2004 | Ellman |
| 6,171,304 | B1 | 1/2001 | Netherly et al. | 6,730,080 B2 | 5/2004 | Harano |
| 6,203,541 | B1 | 3/2001 | Keppel | 6,733,495 B1 | 5/2004 | Bek |

| Patent | Date | Name | | Patent | Date | Name |
|---|---|---|---|---|---|---|
| 6,733,498 B2 | 5/2004 | Paton | | 2004/0138654 A1 | 7/2004 | Goble |
| 6,740,079 B1 | 5/2004 | Eggers | | 2004/0147918 A1 | 7/2004 | Keppel |
| 6,740,085 B2 | 5/2004 | Hareyama | | 2004/0167508 A1 | 8/2004 | Wham et al. |
| 6,758,846 B2 * | 7/2004 | Goble et al. ............ 606/41 | | 2004/0172016 A1 | 9/2004 | Bek |
| 6,783,523 B2 | 8/2004 | Qin | | 2004/0193148 A1 | 9/2004 | Wham et al. |
| 6,784,405 B2 * | 8/2004 | Flugstad et al. ........... 219/497 | | 2004/0230189 A1 | 11/2004 | Keppel |
| 6,786,905 B2 | 9/2004 | Swanson et al. | | 2004/0243120 A1 | 12/2004 | Orszulak et al. |
| 6,790,206 B2 | 9/2004 | Panescu | | 2004/0260279 A1 | 12/2004 | Goble |
| 6,796,981 B2 | 9/2004 | Wham | | 2005/0004564 A1 | 1/2005 | Wham |
| 6,824,539 B2 | 11/2004 | Novak | | 2005/0004569 A1 | 1/2005 | Witt et al. |
| 6,830,569 B2 | 12/2004 | Thompson | | 2005/0021020 A1 | 1/2005 | Blaha et al. |
| 6,843,789 B2 | 1/2005 | Goble | | 2005/0021022 A1 | 1/2005 | Sturm et al. |
| 6,849,073 B2 | 2/2005 | Hoey | | 2005/0033278 A1 * | 2/2005 | McClurken et al. ........... 606/41 |
| 6,855,141 B2 | 2/2005 | Lovewell | | 2005/0101949 A1 | 5/2005 | Harano et al. |
| 6,855,142 B2 | 2/2005 | Harano | | 2005/0101951 A1 | 5/2005 | Wham |
| 6,860,881 B2 | 3/2005 | Sturm | | 2005/0113818 A1 | 5/2005 | Sartor |
| 6,864,686 B2 | 3/2005 | Novak | | 2005/0113819 A1 | 5/2005 | Wham |
| 6,875,210 B2 | 4/2005 | Refior | | 2005/0149151 A1 | 7/2005 | Orszulak |
| 6,893,435 B2 | 5/2005 | Goble | | 2005/0182398 A1 | 8/2005 | Paterson |
| 7,044,948 B2 | 5/2006 | Keppel | | 2005/0197659 A1 | 9/2005 | Bahney |
| 7,044,949 B2 | 5/2006 | Orszulak et al. | | 2005/0203504 A1 | 9/2005 | Wham et al. |
| 7,060,063 B2 | 6/2006 | Marion et al. | | 2006/0025760 A1 | 2/2006 | Podhajsky |
| 7,063,692 B2 | 6/2006 | Sakurai et al. | | 2006/0079871 A1 | 4/2006 | Plaven et al. |
| 7,066,933 B2 | 6/2006 | Hagg | | 2006/0111711 A1 * | 5/2006 | Goble ........................ 606/48 |
| 7,131,860 B2 | 11/2006 | Sartor et al. | | 2006/0161148 A1 | 7/2006 | Behnke |
| 7,137,980 B2 | 11/2006 | Buysse et al. | | 2006/0178664 A1 | 8/2006 | Keppel |
| 7,172,591 B2 | 2/2007 | Harano et al. | | 2006/0224152 A1 | 10/2006 | Behnke et al. |
| 7,247,155 B2 | 7/2007 | Hoey et al. | | 2006/0281360 A1 | 12/2006 | Sartor et al. |
| 7,255,694 B2 | 8/2007 | Keppel | | 2007/0038209 A1 | 2/2007 | Buysse et al. |
| 7,300,435 B2 | 11/2007 | Wham et al. | | 2007/0093800 A1 | 4/2007 | Wham et al. |
| 7,303,557 B2 | 12/2007 | Wham et al. | | 2007/0093801 A1 | 4/2007 | Behnke |
| 2001/0014804 A1 | 8/2001 | Goble et al. | | 2007/0135812 A1 | 6/2007 | Sartor |
| 2001/0029315 A1 | 10/2001 | Sakurai et al. | | 2007/0173802 A1 | 7/2007 | Keppel |
| 2001/0031962 A1 | 10/2001 | Eggleston | | 2007/0173803 A1 | 7/2007 | Wham et al. |
| 2002/0035363 A1 | 3/2002 | Edwards et al. | | 2007/0173804 A1 | 7/2007 | Wham et al. |
| 2002/0035364 A1 | 3/2002 | Schoenman et al. | | 2007/0173805 A1 | 7/2007 | Weinberg et al. |
| 2002/0052599 A1 | 5/2002 | Goble | | 2007/0173806 A1 | 7/2007 | Orszulak et al. |
| 2002/0068932 A1 | 6/2002 | Edwards | | 2007/0173810 A1 | 7/2007 | Orszulak |
| 2002/0107517 A1 | 8/2002 | Witt et al. | | 2007/0173813 A1 | 7/2007 | Odom |
| 2002/0111624 A1 | 8/2002 | Witt et al. | | 2007/0208339 A1 | 9/2007 | Arts et al. |
| 2002/0151889 A1 | 10/2002 | Swanson et al. | | 2007/0225698 A1 | 9/2007 | Orszulak et al. |
| 2002/0193787 A1 | 12/2002 | Qin | | 2007/0250052 A1 | 10/2007 | Wham |
| 2003/0004510 A1 | 1/2003 | Wham et al. | | 2007/0265612 A1 | 11/2007 | Behnke et al. |
| 2003/0060818 A1 | 3/2003 | Kannenberg | | 2007/0282320 A1 | 12/2007 | Buysse et al. |
| 2003/0069571 A1 | 4/2003 | Treat et al. | | 2008/0015563 A1 * | 1/2008 | Hoey et al. ................... 606/34 |
| 2003/0078572 A1 | 4/2003 | Pearson et al. | | | | |
| 2003/0139741 A1 | 7/2003 | Goble et al. | | FOREIGN PATENT DOCUMENTS | | |
| 2003/0153908 A1 | 8/2003 | Goble | | DE | 1099658 | 2/1961 |
| 2003/0163123 A1 | 8/2003 | Goble | | DE | 1139927 | 11/1962 |
| 2003/0163124 A1 | 8/2003 | Goble | | DE | 1149832 | 6/1963 |
| 2003/0171745 A1 | 9/2003 | Francischelli | | DE | 1439302 | 1/1969 |
| 2003/0199863 A1 | 10/2003 | Swanson | | DE | 2439587 | 2/1975 |
| 2003/0225401 A1 | 12/2003 | Eggers et al. | | DE | 2455174 | 5/1975 |
| 2004/0002745 A1 | 1/2004 | Flemming | | DE | 2407559 | 8/1975 |
| 2004/0015163 A1 | 1/2004 | Buysse et al. | | DE | 2602517 | 7/1976 |
| 2004/0015216 A1 | 1/2004 | DeSisto | | DE | 2504280 | 8/1976 |
| 2004/0019347 A1 | 1/2004 | Sakurai | | DE | 2540968 | 3/1977 |
| 2004/0024395 A1 | 2/2004 | Ellman | | DE | 2820908 | 11/1978 |
| 2004/0030328 A1 | 2/2004 | Eggers | | DE | 2803275 | 8/1979 |
| 2004/0030330 A1 | 2/2004 | Brassell et al. | | DE | 2823291 | 11/1979 |
| 2004/0044339 A1 | 3/2004 | Beller | | DE | 2946728 | 5/1981 |
| 2004/0049179 A1 | 3/2004 | Francischelli | | DE | 3143421 | 5/1982 |
| 2004/0054365 A1 | 3/2004 | Goble | | DE | 3045996 | 7/1982 |
| 2004/0059323 A1 | 3/2004 | Sturm et al. | | DE | 3120102 | 12/1982 |
| 2004/0068304 A1 | 4/2004 | Paton | | DE | 3510586 | 10/1986 |
| 2004/0082946 A1 | 4/2004 | Malis | | DE | 3604823 | 8/1987 |
| 2004/0095100 A1 | 5/2004 | Thompson | | DE | 390937 | 4/1989 |
| 2004/0097912 A1 | 5/2004 | Gonnering | | DE | 3904558 | 8/1990 |
| 2004/0097914 A1 | 5/2004 | Pantera | | DE | 3942998 | 7/1991 |
| 2004/0097915 A1 | 5/2004 | Refior | | DE | 4339049 A1 | 5/1995 |
| 2004/0116919 A1 | 6/2004 | Heim | | DE | 19717411 A1 | 11/1998 |
| 2004/0133189 A1 | 7/2004 | Sakurai | | DE | 19848540 A1 | 5/2000 |
| 2004/0138653 A1 | 7/2004 | Dabney et al. | | | | |

| | | |
|---|---|---|
| EP | 246350 | 11/1987 |
| EP | 310431 | 4/1989 |
| EP | 325456 | 7/1989 |
| EP | 390937 | 10/1990 |
| EP | 556705 | 8/1993 |
| EP | 0569130 A1 | 11/1993 |
| EP | 608609 | 8/1994 |
| EP | 0694291 | 1/1996 |
| EP | 836868 | 4/1998 |
| EP | 336742 | 10/1998 |
| EP | 878169 | 11/1998 |
| EP | 1051948 | 11/2000 |
| EP | 1151725 | 11/2001 |
| EP | 1293171 | 3/2003 |
| EP | 1495712 | 1/2005 |
| EP | 1500378 | 1/2005 |
| EP | 1535581 | 6/2005 |
| EP | 0880220 B1 | 6/2006 |
| EP | 1707143 | 10/2006 |
| EP | 1810630 | 7/2007 |
| FR | 1275415 | 10/1961 |
| FR | 1347865 | 11/1963 |
| FR | 2313708 | 12/1976 |
| FR | 2502935 | 10/1982 |
| FR | 2517953 | 6/1983 |
| FR | 2573301 | 5/1986 |
| GB | 607850 | 9/1948 |
| GB | 855459 | 11/1960 |
| GB | 902775 | 8/1962 |
| GB | 2164473 | 3/1986 |
| GB | 2214430 | 9/1989 |
| GB | 2358934 A | 8/2001 |
| SU | 166452 | 1/1965 |
| SU | 727201 | 4/1980 |
| SU | 727202 | 4/1980 |
| WO | WO92/06642 | 4/1992 |
| WO | WO93/24066 | 12/1993 |
| WO | WO94/24949 | 11/1994 |
| WO | WO94/28809 | 12/1994 |
| WO | WO95/09577 | 4/1995 |
| WO | WO95/19148 | 7/1995 |
| WO | WO96/02180 | 2/1996 |
| WO | WO96/04860 | 2/1996 |
| WO | WO96/08794 | 3/1996 |
| WO | WO96/18349 | 6/1996 |
| WO | WO96/29946 | 10/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/17029 | 5/1997 |
| WO | WO01/00114 | 1/2001 |
| WO | WO02/07627 | 1/2002 |
| WO | WO02/11634 | 2/2002 |
| WO | WO02/45589 | 6/2002 |
| WO | WO02/47565 | 6/2002 |
| WO | WO02/088128 | 7/2002 |
| WO | WO03/090635 | 11/2003 |
| WO | WO03/092520 | 11/2003 |
| WO | WO2004/028385 | 4/2004 |
| WO | WO2005/046496 | 5/2005 |
| WO | WO2005/048809 | 6/2005 |
| WO | WO2005/050151 | 6/2005 |
| WO | WO2005048809 A1 | 6/2005 |
| WO | WO2005/060849 | 7/2005 |

OTHER PUBLICATIONS

Valleylab Brochure "Valleylab Electroshield Monitoring System" 2 pp. Nov. 1995.
Richard Wolf Medical Instruments Corp. Brochure, "Kleppinger Bipolar Forceps & Bipolar Generator" 3 pp. Jan. 1989.
Bergdahl et al. "Studies on Coagulation and the Development of an Automatic Computerized Bipolar Coagulator" J.Neurosurg, vol. 75, Jul. 1991, pp. 148-151.
International Search Report PCT/US03/37110 dated Jul. 25, 2005.
International Search Report PCT/US03/37310 dated Aug. 13, 2004.
International Search Report EP 04009964 dated Jul. 13, 2004.
International Search Report EP 98300964.8 dated Dec. 4, 2000.
International Search Report EP 04015981.6 dated Sep. 29, 2004.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5. dated Apr. 21, 2008.
International Search Report—Extended EP 06000708.5 dated Aug. 22, 2006.
International Search Report EP 05002769.7 dated Jun. 9, 2006.
International Search Report EP 06006717.0 dated Aug. 7, 2006.
Ni W et al: "A Signal Processing Method for the Coriolis Mass Flowmeter Based on a Normalized . . . " Journal of Applied Sciences—Yingyong Kexue Xuebao, Shanghai CN, vol. 23 No. 2;(Mar. 2005); 160-164.
International Search Report EP06022028.2 dated Feb. 5, 2007.
International Search Report EP06025700.3 dated Apr. 12, 2007.
International Search Report EP07001481.6 dated Apr. 23, 2007.
International Search Report EP07001485.7 dated May 15, 2007.
International Search Report EP07001527.6 dated May 9, 2007.
International Search Report EP07004355.9 dated May 21, 2007.
International Search Report EP05004431.2 dated Jun. 2, 2005.
Muller et al., "Extended Left Hemicolectomy Using the LigaSure Vessel Sealing System" Innovations That Work; Sep. 1999.
International Search Report EP 07008207.8. dated Sep. 5, 2007.
International Search Report EP 07010673.7 dated Sep. 24, 2007.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994) pp. 297-307.
Astrahan, "A Localized Current Field Hyperthermia System for Use with 192-tridium Interstitial Implants" Medical Physics, 9 (3), May/Jun. 1982.
Bergdahl et al., "Studies on Coagulation and the Development of an Automatic computerized Bipolar Coagulator" Journal of Neurosurgery 75:1, (Jul. 1991) pp. 148-151.
Chicharo et al. "A Sliding Goertzel Algorith" Aug. 1996, pp. 283-297 Signal Processing, Elsevier Science Publishers B.V. Amsterdam, NL vol. 52 No. 3.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and Its Effect on Tissue Impedance" Applied Neurophysiology 51: (1988) pp. 230-242.
Cosman et al., "Theoretical Aspects of Radiofrequency Lesions in the Dorsal Root Entry Zone" Neurosurgery 15:(1984) pp. 945-950.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure "The O.R. Pro 300" 1p.
Ogden Goertzel Alternative to the Fourier Transform: Jun. 1993 pp. 485-487 Electronics World; Reed Business Publishing, Sutton, Surrey, BG vol. 99, No. 9. 1687.
Sugita at al., "Bipolar Coagulator with Automatic Thermocontrol" J. Neurosurg., vol. 41, Dec. 1944, pp. 777-779.
Valleylab Brochure "Valleylab Electroshield Monitoring System" 2 pp.
Vallfors et al., "Automatically Controlled Bipolar Electrosoagulation-'COA-COMP'" Neurosurgical Review 7:2-3 (1984) pp. 187-190.
Wald et al., "Accidental Burns", JAMA, Aug. 16, 1971, vol. 217, No. 7, pp. 916-921.

Richard Wolf Medical Instruments Corp. Brochure, "Kleppinger Bipolar Forceps & Bipolar Generator" 3 pp.
International Search Report PCT/US03/37110, Jul. 25, 2005.
International Search Report PCT/US03/37310, Aug. 13, 2004.
International Search Report EP 04009964, Jul. 28, 2004.
International Search Report EP 98300964.8, Dec. 13, 2000.
International Search Report EP 04015981.6, Oct. 15, 2004.

* cited by examiner

VESSEL SEALING SYSTEM USING CAPACITIVE RF DIELECTRIC HEATING

PRIORITY

This application claims priority to an application entitled "VESSEL SEALING SYSTEM USING CAPACITIVE RF DIELECTRIC HEATING" filed in the United States Patent and Trademark Office on Mar. 2, 2004 and assigned Ser. No. 60/549,232, the contents of which are hereby incorporated by reference.

BACKGROUND

1. Technical Field

The present disclosure is directed to electrosurgical systems, and, in particular, to an electrosurgical system for vessel sealing using capacitive radio frequency (RF) dielectric heating.

2. Description of the Related Art

Electrosurgical generators are employed by surgeons in conjunction with an electrosurgical tool to cut, coagulate, desiccate and/or seal patient tissue. High frequency electrical energy, e.g., radio frequency (RF) energy, is produced by the electrosurgical generator and applied to the tissue by the electrosurgical tool. Both monopolar and bipolar configurations are commonly used during electrosurgical procedures.

Electrosurgical generators typically include power supply circuits, front panel interface circuits, and RF output stage circuits. Many electrical designs for electrosurgical generators are known in the field. In certain electrosurgical generator designs, the RF output stage can be adjusted to control the RMS (root mean square) output power. The methods of controlling the RF output stage may include changing the duty cycle, or changing the amplitude of the driving signal to the RF output stage. The method of controlling the RF output stage is described herein as changing an input to the RF output stage.

Electrosurgical techniques have been used to seal or fuse small diameter blood vessels, vascular bundles and tissue. In this application, two layers of tissue are grasped and clamped together while electrosurgical power is applied. By applying a unique combination of pressure, gap distance between opposing seal surfaces and controlling the electrosurgical energy, the two tissue layers are welded or fused together into a single mass with limited demarcation between tissue layers. Tissue fusion is similar to vessel sealing, except that a vessel or duct is not necessarily sealed in this process. For example, tissue fusion may be used instead of staples for surgical anastomosis.

One of the issues associated with electrosurgical sealing or fusion of tissue is undesirable collateral damage to tissue due to the various thermal effects associated with electrosurgically energizing tissue. The tissue at the operative site is heated by electrosurgical current typically applied by the electrosurgical instrument. Healthy tissue adjacent to the operative site may become thermally damaged if too much heat is allowed to build up at the operative site or adjacent the sealing surfaces. For example, during sealing, the heat may conduct or spread to the adjacent tissue and cause a significant region of tissue necrosis. This is known as thermal spread. Thermal spread becomes important when electrosurgical instruments are used in close proximity to delicate anatomical structures. Therefore, an electrosurgical generator that reduces the possibility of thermal spread would offer a better opportunity for a successful surgical outcome.

Another issue associated with electrosurgical tissue sealing or tissue fusion is the buildup of eschar on the surgical instrument. Eschar is a deposit which is created from tissue that is charred by heat. Surgical tools often lose effectiveness when coated with eschar.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. It has been determined that a fused vessel wall is optimum between about 0.001 and about 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

As mentioned above, in order to properly and effectively seal larger vessels, a greater closure force between opposing jaw members is required. It is known that a large closure force between the jaws typically requires a large moment about the pivot for each jaw. This presents a challenge because the jaw members are typically affixed with pins which are positioned to have a small moment arms with respect to the pivot of each jaw member. A large force, coupled with a small moment arm, is undesirable because the large forces may shear the pins. As a result, designers must compensate for these large closure forces by either designing instruments with metal pins and/or by designing instruments which at least partially offload these closure forces to reduce the chances of mechanical failure. As can be appreciated, if metal pivot pins are employed, the metal pins must be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit or arcing between the electrodes, and a small closure force may cause pre-mature movement of the tissue during compression and prior to activation.

Thus, a need exists to develop an electrosurgical system which effectively seals vascular tissue and solves the aforementioned problems by providing an instrument which enables a large closure force between the opposing jaws members, reduces the chances of short circuiting the opposing jaws during activation and reduces the possibility of thermal spread.

SUMMARY

An electrosurgical system for sealing vessels using capacitive (RF) dielectric heating and a method thereof are provided. The present disclosure provides a system and method where tissue sealing is caused by capacitive heating, along with pressure and time. The system includes an electrosurgical tool or instrument having an end effector with parallel plate electrodes that will clamp onto a vessel, or tissue, and maintain a specified gap distance; however, the electrodes will be coated with a non-conductive dielectric material. Such an end effector will ensure that direct conduction between the electrodes does not occur through tissue or fluids and effectively creates a parallel plate capacitor with a dielectric, e.g., tissue and coating, in between the plates. The electrosurgical instrument will be activated with an AC signal at a specified RF frequency, e.g., a Debye resonance frequency, via an electrosurgical generator. An effective AC current will flow through the tissue and cause heating due to frictional losses from rotating polar molecules in the tissue.

Advantageously, the capacitive RF dielectric system of the present disclosure will provide more uniform heating, e.g., reduced thermal spread, due to a more uniform electric field generated between the electrodes than with a conventional ohmic heating system and will eliminate arcing since there will be no direct conduction between electrodes. Additionally, a more accurate temperature measurement is achieved with a single temperature sensor due to the uniform heat distribution. Furthermore, since the surface contacting tissue will be coated with a, preferably, non-stick, dielectric material, tissue sticking to the end effector will be reduced.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the present disclosure will be described herein below with reference to the accompanying drawings. In the following description, well-known functions or constructions are not described in detail to avoid obscuring the disclosure in unnecessary detail. In the figures, like reference numerals represent like elements.

An electrosurgical system for sealing vessels using capacitive (RF) dielectric heating and a method thereof are provided. Capacitive RF dielectric heating is employed in an electrosurgical system to heat/desiccate tissue for sealing purposes. Generally, a high voltage RF frequency AC signal is applied to a set of parallel electrodes on opposite sides of a dielectric, e.g., tissue or electrode coatings, forming a capacitive circuit. A tissue to be sealed is sandwiched or placed between the electrodes so that an AC displacement current flows through the tissue as a result of polar molecules in the tissue aligning and rotating in opposite fashion to the applied AC electric field. Direct conduction does not occur but instead an effective AC current flows through the parallel electrodes due to polar molecules with effective charges rotating back and forth. Heating occurs because these polar molecules encounter interactions with neighboring molecules resulting in lattice and frictional losses as they rotate. Since the internal polar molecules of the tissue are being heated, the system does not rely on thermal conduction and does not require electrodes to contact a surface of the tissue as in conventional ohmic heating systems. The combination of the heat generated, along with pressure applied and a specified gap distance, will effectively seal the tissue held between the electrodes.

Figure 1:
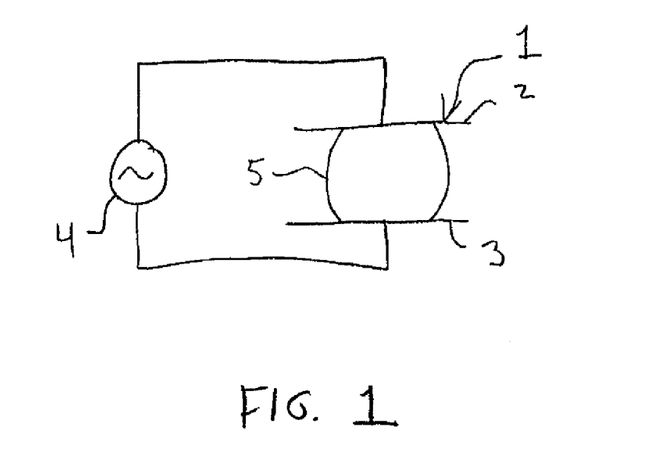
FIG. 1 is a schematic diagram illustrating the principles of one embodiment of the present disclosure.

An exemplary electrical equivalent circuit of the principle described above is shown in FIG. 1 as a capacitor 1 having parallel electrodes 2, 3 coupled to an RF energy source 4, the parallel electrodes 2, 3 being placed around a medium 5, e.g., a dielectric, to be heated. Voltage losses of the dielectric increase as the frequency of the applied signal is increased due to higher speed interactions with the neighboring molecules. The higher the frequency of the alternating field the greater the energy imparted into the medium 5, e.g. tissue, until the frequency is so high that the rotating molecules can no longer keep up with the external field due to lattice limitations. The frequency at which that occurs is called a "Debye resonance" and is the frequency at which the maximum energy can be imparted into a medium for a given electric field strength and, therefore, the maximum heating. This high frequency limitation is inversely proportional to the complexity of the polar molecule. For example, proteins with amino acid polar side groups or chains have a slower rotation limitation, and thus lower Debye resonance, than simple polar water molecules. These Debye resonance frequencies also shift with temperature as the medium 5 is heated.

In the electrosurgical system of the present disclosure, the RF frequency or composite signal of several RF frequencies are selected to correlate with the dominant Debye resonance frequency groups of the tissue that is being heated. These Debye resonances are dependent on the polar molecular makeup of the tissue and thus a plurality of tissue types may be researched for different Debye resonance frequencies to be stored in the electrosurgical system to appropriately heat a selected tissue.

The system is constructed to provide an AC RF signal displacement current at an RF frequency in the range of 3 MHz to 300 MHz. This range includes the HF (3 MHz to 30 MHz) and VHF (30 MHz to 300 MHz) frequencies in the lower regions of the radio frequency (RF) range. Superior results are achieved by operating in the frequency range of 3 MHz-30 MHz.

The frequency or composite frequency groups of the RF signal used in the electrosurgical system will track with and change with temperature to account for the fact that the Debye resonance frequencies of the polar molecular constituents of the tissue also shift with temperature.

It is contemplated that the RF signal power level and electric field strength can be adjusted automatically by a computer control system which changes the load current to control heating rates and account for different tissue types. The power level is controlled by measuring the current and field strength across the load. The voltage (AC field strength) is then adjusted, which in turn varies the current, until measurements of the current and field strength indicate that the desired power level has been achieved.

Figure 2:
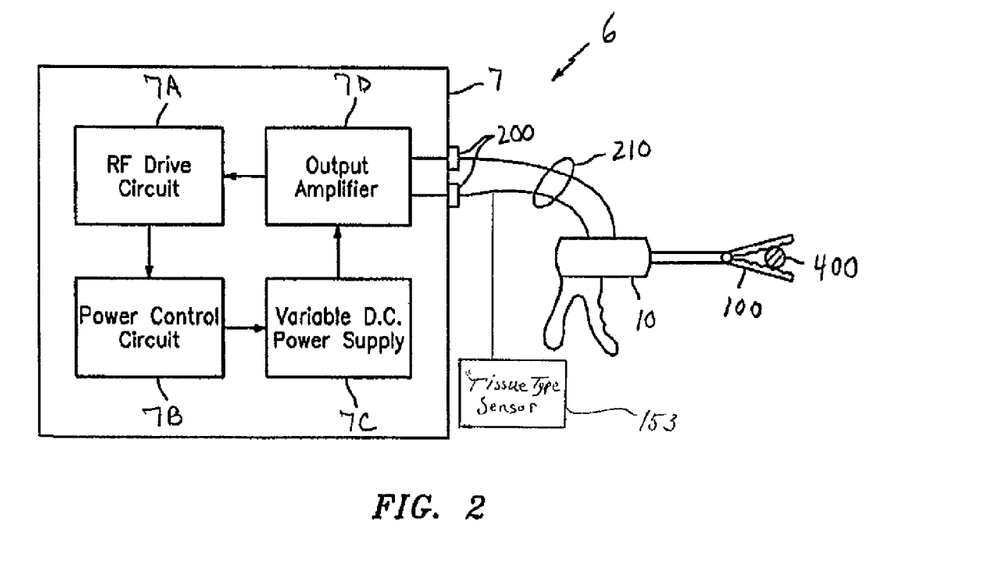
FIG. 2 is a simplified block diagram of an electrosurgical system which may be used with the present disclosure.

An electrosurgical system 6, which can be used to practice this disclosure, is shown in FIG. 2. The system 6 can be used for sealing vessels 400 and other tissues including ducts, veins, arteries and vascular tissue. The system 6 includes an electrosurgical generator 7 and a surgical tool, also referred to herein as a surgical instrument 10. The surgical instrument 10 is illustrated by way of example, and as will become apparent from the discussion below, other instruments can be utilized. The electrosurgical generator 6 includes several interconnected sub-units, including an RF drive circuit 7A, a power control circuit 7B, a variable D.C. power supply 7C and an output amplifier 7D. The surgical instrument 10 is electrically connected to the electrosurgical generator 7 using a plug 200 for receiving controlled electrosurgical power therefrom. The surgical instrument 10 has some type of end effector member 100, such as a forceps or hemostat, capable of grasping and holding the vessels and tissues of the patient. The member 100, also referred to simply as end effector 100, is assumed, in this embodiment, to be capable of applying and maintaining a relatively constant level of pressure on the vessel 400.

The member 100 is provided in the form of bipolar electrosurgical forceps using two generally opposing electrodes disposed on inner opposing surfaces of the member 100, and which are both electrically coupled to the output of the electrosurgical generator 7. During use, different electric potentials are applied to each electrode. When the forceps are utilized to clamp or grasp the vessel 400 therebetween, the electrical energy output from the electrosurgical generator 7 is transferred through the intervening tissue. Both open surgical procedures and endoscopic surgical procedures can be performed with suitably adapted surgical instruments 10. It should also be noted that the member 100 could be monopolar forceps that utilize one active electrode, with the other (return) electrode or pad being attached externally to the patient, or a combination of bipolar and monopolar forceps.

Figure 3:
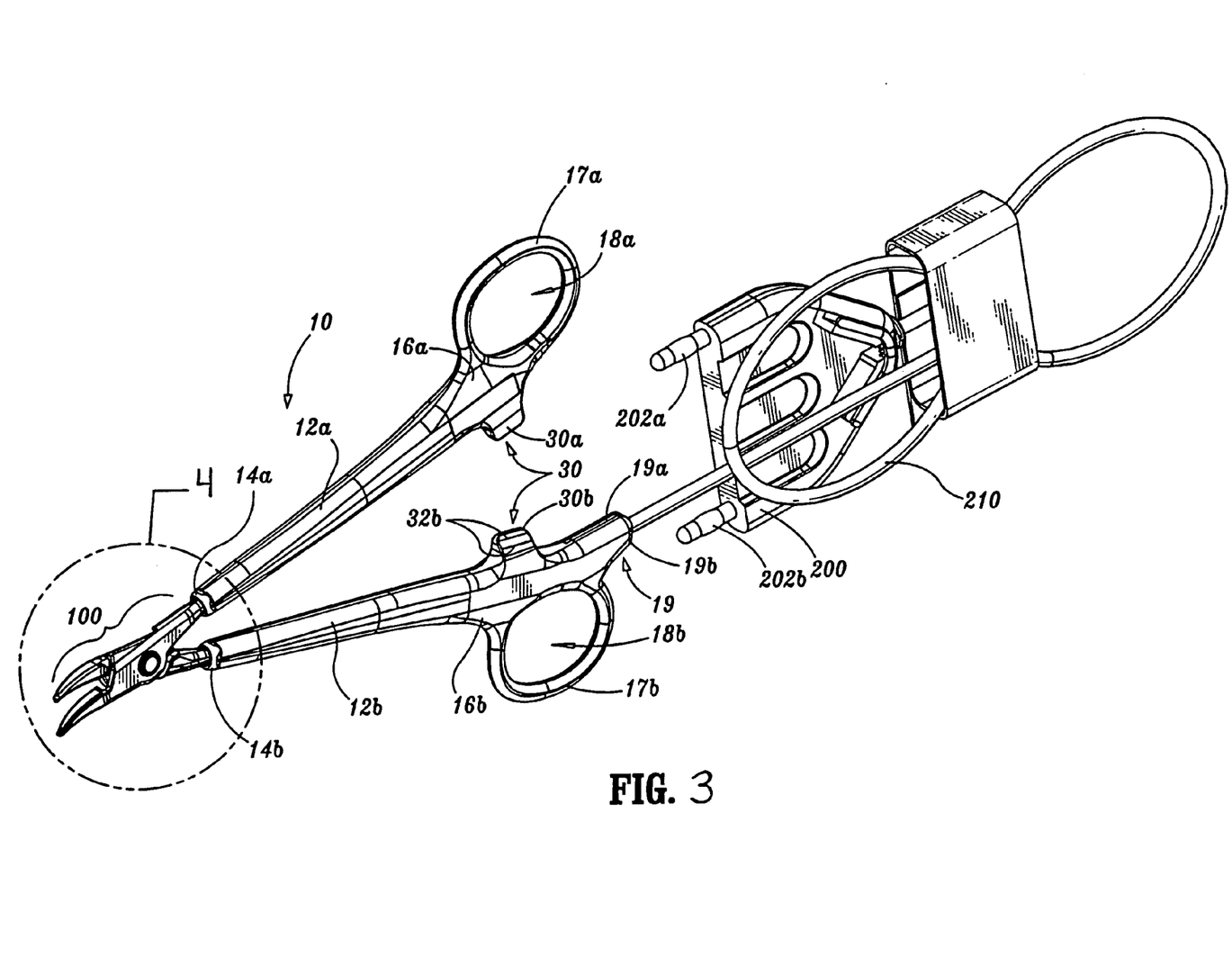
FIG. 3 is a perspective view of one embodiment of a surgical instrument having bipolar forceps which may be configured according to the present disclosure.
Figure 4:
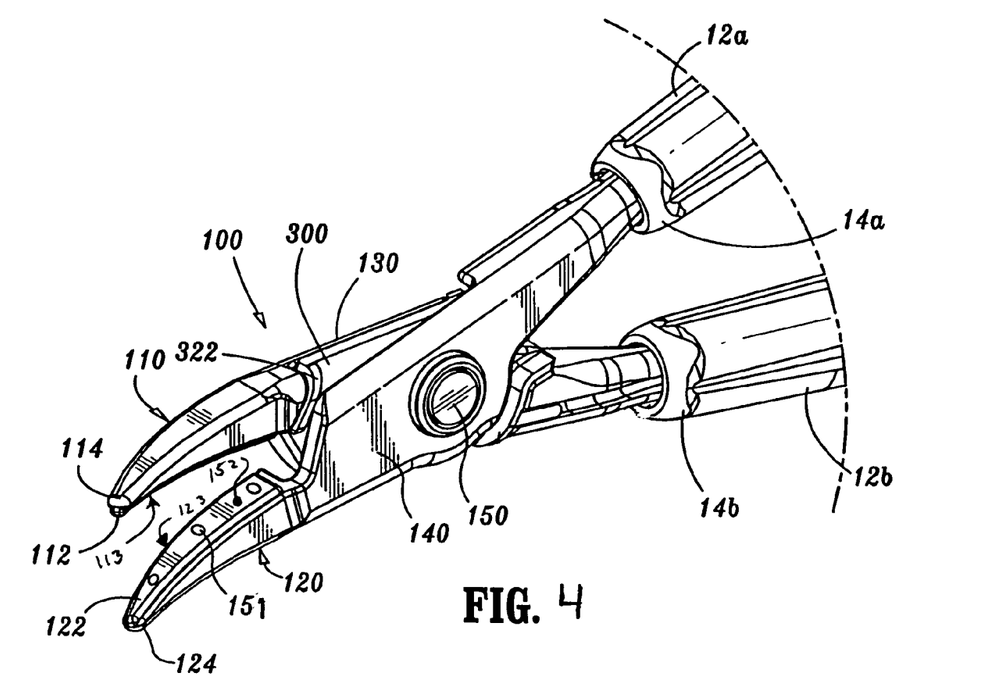
FIG. 4 is an enlarged, perspective view of the end effector assembly of the forceps of FIG. 3 shown in an open configuration.
Figure 5:
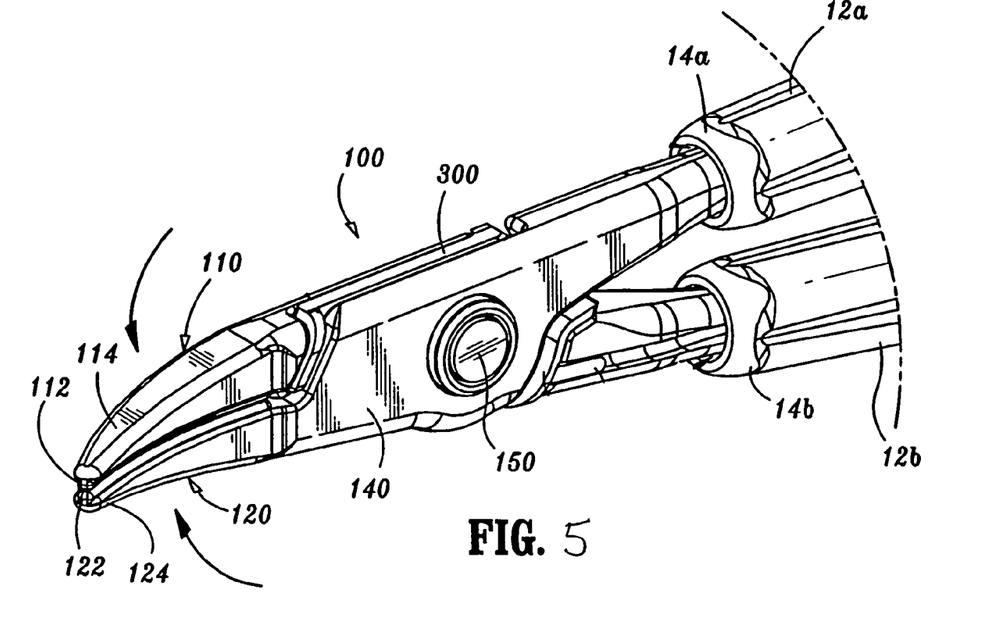
FIG. 5 is an enlarged, perspective view of the end effector assembly of the forceps of FIG. 3 shown in a closed configuration.

By way of further explanation, FIG. 3 is a perspective view of one embodiment of the surgical instrument 10 having a bipolar end effector implemented as forceps 100 while FIGS. 4 and 5 are enlarged, perspective views of a distal end of the bipolar forceps 100 shown in FIG. 3.

Referring now to FIGS. 3-6, a forceps 10 for use with open surgical procedures includes elongated shaft portions 12a and 12b each having a proximal end 16a and 16b, respectively, and a distal end 14a and 14b, respectively. In the drawings and in the descriptions which follow, the term "proximal", as is traditional, will refer to the end of the forceps 10 which is closer to the user, while the term "distal" will refer to the end which is further from the user.

The forceps 10 includes an end effector assembly 100 which attaches to distal ends 14a and 14b of shafts 12a and 12b, respectively. As explained in more detail below, the end effector assembly 100 includes pair of opposing jaw members 110 and 120 which are pivotably connected about a pivot pin 150.

Preferably, each shaft 12a and 12b includes a handle 17a and 17b disposed at the proximal end 16a and 16b thereof which each define a finger hole 18a and 18b, respectively, therethrough for receiving a finger of the user. As can be appreciated, finger holes 18a and 18b facilitate movement of the shafts 12a and 12b relative to one another which, in turn, pivot the jaw members 110 and 120 from an open position (FIG. 4) wherein the jaw members 110 and 120 are disposed in spaced relation relative to one another to a clamping or closed position (FIG. 5) wherein the jaw members 110 and 120 cooperate to grasp tissue 400 (FIG. 6) therebetween.

Figure 6:
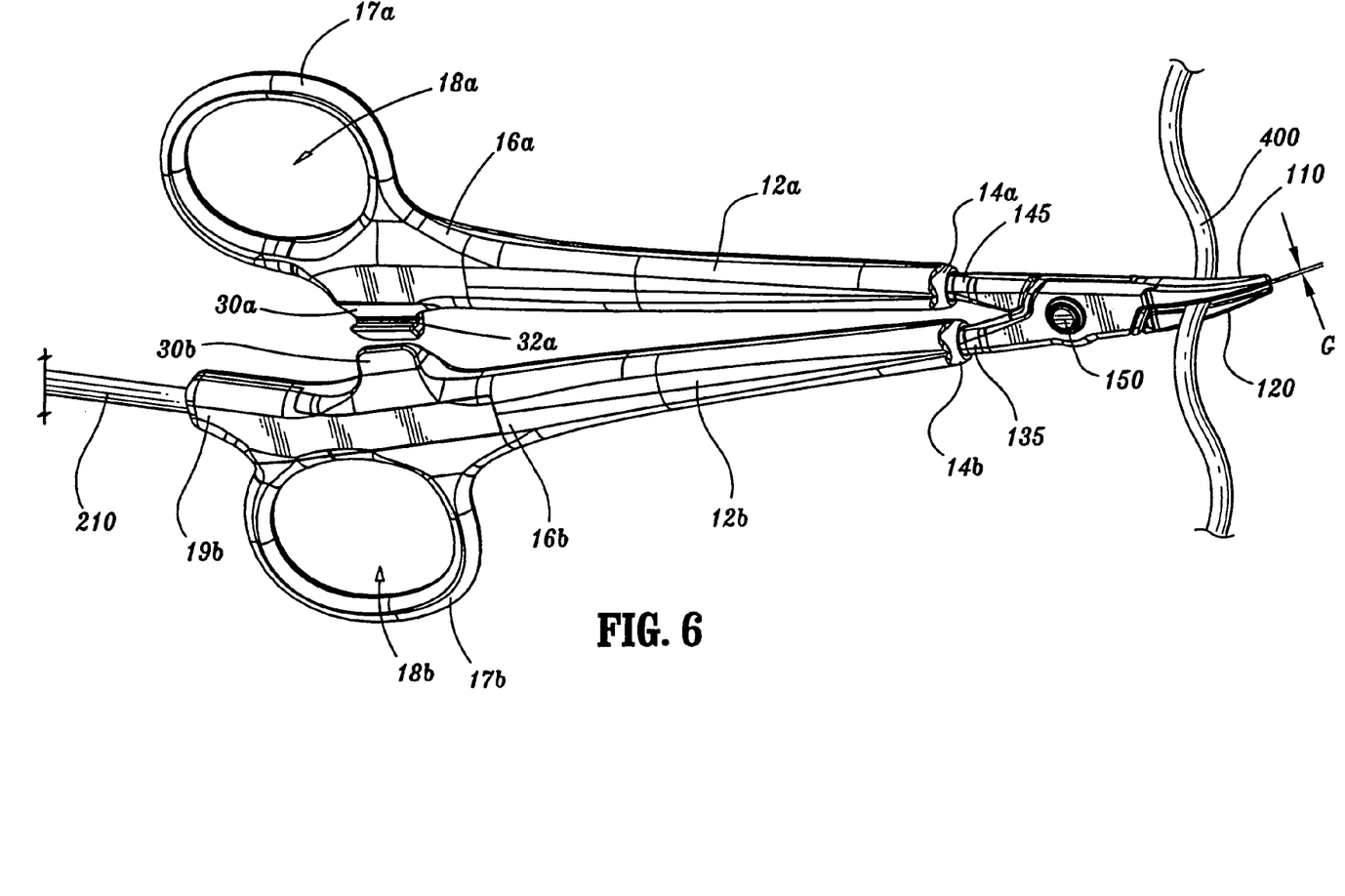
FIG. 6 is a right, perspective view of the forceps of FIG. 3 shown grasping tissue.

A ratchet 30 is preferably included for selectively locking the jaw members 110 and 120 relative to one another at various positions during pivoting. As best shown in FIG. 6, a first ratchet interface, e.g., 30a, extends from the proximal end 16a of shaft member 12a towards a second ratchet interface 30b in a generally vertically aligned manner such that the inner facing surfaces of each ratchet 30a and 30b abut one another upon closure about the tissue 400. Preferably, each ratchet interface 30a and 30b includes a plurality of flanges 32a and 32b, respectively, which project from the inner facing surface of each ratchet interface 30a and 30b such that the ratchet interfaces 30a and 30b interlock in at least one position. In the embodiment shown in FIG. 6, the ratchet interfaces 30a and 30b interlock at several different positions.

Preferably, each position associated with the cooperating ratchet interfaces 30a and 30b holds a specific, i.e., constant, strain energy in the shaft members 12a and 12b which, in turn, transmits a specific closing force to the jaw members 110 and 120. It is envisioned that the ratchet 30 may include graduations or other visual markings which enable the user to easily and quickly ascertain and control the amount of closure force desired between the jaw members. A design without a ratchet system or similar system would require the user to hold the jaw members 110 and 120 together by applying constant force to the handles 17a and 17b which may yield inconsistent results.

As best illustrated in FIG. 3, one of the shafts, e.g., 12b, includes a proximal shaft connector 19 which is designed to connect the forceps 10 to a source of electrosurgical energy such as an electrosurgical generator 7, which will be described below in detail. More particularly, proximal shaft connector 19 is formed by a cover 19a and a flange 19b which extends proximally from shaft 12b. Preferably, cover 19a and flange 19b mechanically cooperate to secure an electrosurgical cable 210 to the forceps 10 such that the user may selectively apply electrosurgical energy as needed.

The proximal end of the cable 210 includes a plug 200 having a pair of prongs 202a and 202b which are dimensioned to electrically and mechanically engage the electrosurgical energy generator. The interior of cable 210 houses at least a pair of leads which conduct the different electrical potentials from the electrosurgical generator to the jaw members 110 and 120. The cable 210 may also include a plurality of other leads coupled to sensors, e.g., a temperature sensor, voltage sensor, current sensor, tissue type sensor, etc., for providing feedback to the electrosurgical generator 7, as explained in greater detail below. FIG. 2 shows a tissue type sensor 153 for determining a type of tissue to be sealed coupled to the generator 7 via cable 210 to provide tissue type feedback to the generator as will be described below.

As best seen in FIGS. 4 and 5, the two opposing jaw members 110 and 120 of the end effector assembly 100 are pivotable about pin 150 from the open position to the closed position for grasping tissue 400 therebetween. Jaw members 110 and 120 are generally symmetrical and include similar component features which cooperate to permit facile rotation about pivot pin 150 to effect the grasping and sealing of tissue 400. As a result and unless otherwise noted, jaw member 110 and the operative features associated therewith will initially be described herein in detail and the similar component features with respect to jaw member 120 will be briefly summarized thereafter.

Jaw member 110 includes an insulated outer housing 114 which is dimensioned to mechanically engage an electrode 112 and a proximally extending flange 130 which is dimensioned to seat a distal connector 300. Preferably, outer insulative housing 114 extends along the entire length of jaw member 110 to reduce alternate or stray current paths during sealing and/or incidental burning of tissue 400. The inner facing surface of flange 130 includes an electrically conductive plate which conducts electrosurgical energy to the electrode 112 upon activation.

Likewise, jaw member 120 include similar elements which include: an outer housing 124 which engages an electrode 122; a proximally extending flange 140 which seats the opposite face of the distal connector 300; an electrically conductive plate which conducts electrosurgical energy to the electrode 122 upon activation.

Each electrode 112, 122 of the first and second jaw members will be coated with a non-conductive dielectric material 113, 123 that itself will not be heated since the dielectric material will be selected to have a Debye resonance at much higher frequency then a Debye resonance of the tissue to be sealed. Advantageously, the dielectric material will increase the dielectric constant of the gaps between the electrodes 112, 122 and the tissue 400 to be heated thus improving energy transfer to the tissue 400.

Preferably, the dielectric material 113, 123 is molded onto the jaw members 110, 120 (e.g., overmolding, injection molding, etc.), stamped onto the jaw members 110, 120 or deposited (e.g., deposition) onto the jaw members 110, 120. The dielectric material may also be pre-formed and slideably attached to the jaw members and/or attached to the electrodes 112, 112 in a snap-fit manner. Other techniques involve thermally spraying the dielectric material onto the surface of the jaw member 110, 120. Alternatively, the dielectric material 113, 123 can be molded onto the inner-facing surface of the jaw members 110, 120 or, in some cases, it may be preferable to adhere the dielectric material to the inner facing surfaces of the jaw members 110, 120 by any known method of adhesion.

Preferably, the dielectric material is a material having superior non-stick properties, for example, KAPTON®, polytetrafluoroethylene (PTFE), etc., which will reduce the amount of tissue that sticks to the end effector and thus improves the overall efficacy of the instrument. KAPTON® is a polyimide film commercially available from Dupont of Wilmington, Del.

Since the Debye resonance frequency of the tissue will shift with a change in temperature of the tissue, the end effector 100 will include at least one temperature sensor 152. The temperature sensor 152 may be any known temperature sensor in the art, for example, a thermocouple, thermistor, resistance temperature detector (RTD), semiconductor temperature device, infrared temperature sensor, etc. The temperature sensor 152 will be coupled to the generator 7 via cable 210 to provide temperature feedback to the generator as will be described below.

It is envisioned that one of the jaw members, e.g., 120, includes at least one stop member 151 disposed on an inner facing surface of the electrode surface 112 (and/or 122). Alternatively or in addition, the stop member 151 may be positioned adjacent to the electrode 112, 122 or proximate the pivot pin 150. The stop member(s) is preferably designed to facilitate gripping and manipulation of tissue 400 and to define a gap "G" (FIG. 6) between opposing jaw members 110 and 120 during sealing. Preferably the separation distance during sealing or the gap distance "G" is within the range of about 0.001 inches (~0.03 millimeters) to about 0.006 inches (~0.16 millimeters).

A detailed discussion of these and other envisioned stop members 151 as well as various manufacturing and assembling processes for attaching, disposing, depositing and/or affixing the stop members 151 to the electrodes surfaces 112, 122 are described in commonly-assigned, co-pending PCT Application Ser. No. PCT/US01/11222 entitled "BIPOLAR ELECTROSURGICAL FORCEPS WITH NON-CONDUCTIVE STOP MEMBERS" which is hereby incorporated by reference in its entirety herein.

Figure 7:
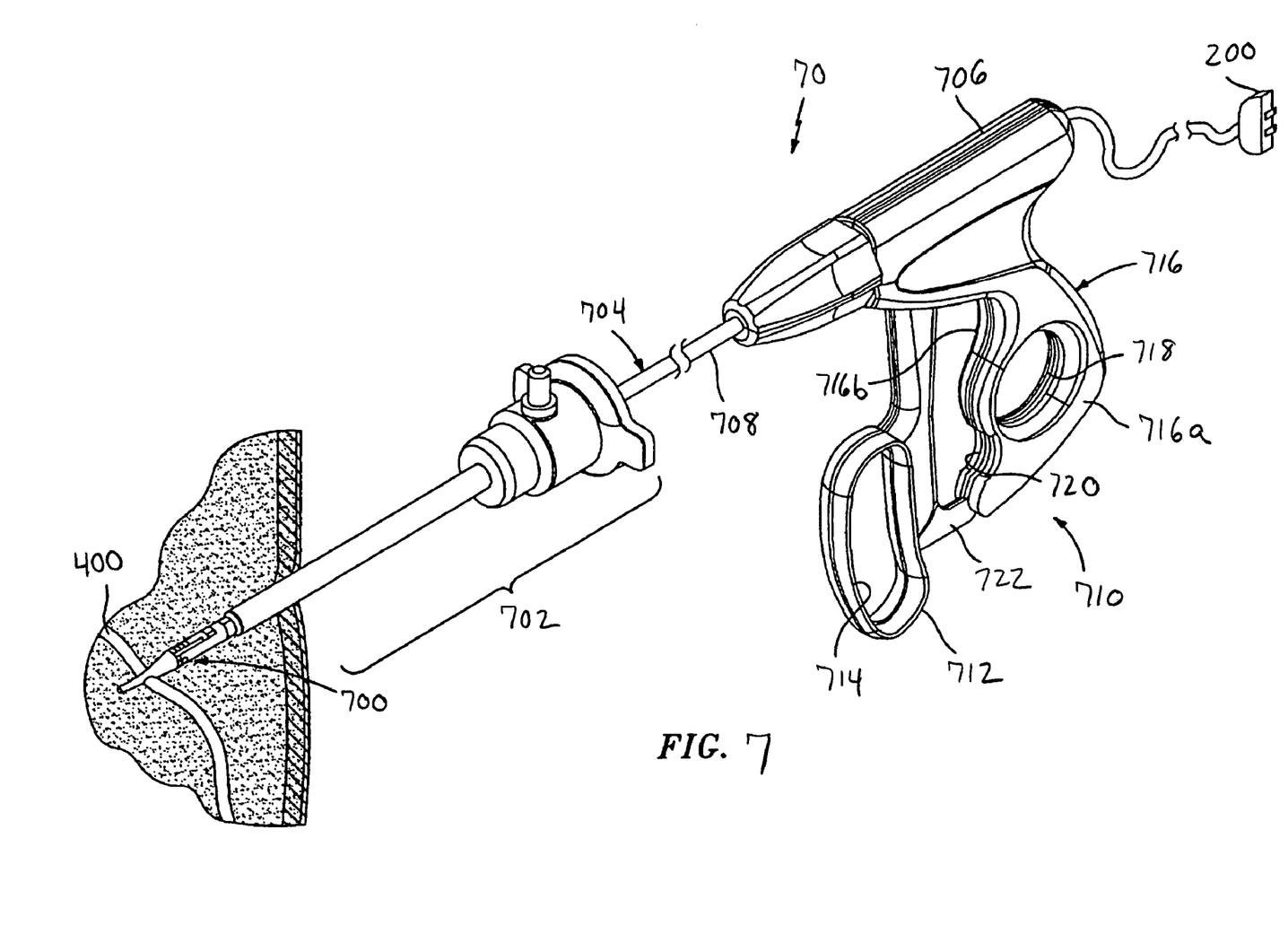
FIG. 7 is a perspective view of an endoscopic forceps which may be configured according to the present disclosure.

FIG. 7 is a perspective view of another embodiment of a surgical instrument 70 having end effector members or forceps 700 that are suitable for an endoscopic surgical procedure. The end effector member 700 is depicted as sealing the tubular vessel 400 through a cannula assembly 702.

The surgical instrument 70 for use with endoscopic surgical procedures includes a drive rod assembly 704 which is coupled to a handle assembly 706. The drive rod assembly 704 includes an elongated hollow shaft portion 708 having a proximal end and a distal end. An end effector assembly 700 is attached to the distal end of shaft 708 and includes a pair of opposing jaw members. Preferably, handle assembly 706 is attached to the proximal end of shaft 708 and includes an activator 710 for imparting movement of the forceps jaw members of end effector member 700 from an open position, wherein the jaw members are disposed in spaced relation relative to one another, to a clamping or closed position, wherein the jaw members cooperate to grasp tissue therebetween.

Similar to end effector 100, end effector 700 will include first and second jaw members, each having an electrode for imparting electrosurgical energy to tissue 400. Each electrode will be coated with a non-conductive dielectric material as described above in reference to end effector 100. Alternatively, a non-conductive pad may be selectively mounted atop the inner facing surface of each electrode or the electrodes may be manufactured with the pad mounted thereon.

Activator 710 includes a movable handle 712 having an aperture 714 defined therein for receiving at least one of the operator's fingers and a fixed handle 716 having an aperture 718 defined therein for receiving an operator's thumb. Movable handle 712 is selectively moveable from a first position relative to fixed handle 716 to a second position in the fixed handle 716 to close the jaw members. Preferably, fixed handle 716 includes a channel 720 which extends proximally for receiving a ratchet 722 which is coupled to movable handle 712. This structure allows for progressive closure of the end effector assembly, as well as a locking engagement of the opposing jaw members. In some cases it may be preferable to include other mechanisms to control and/or limit the movement of handle 712 relative to handle 716 such as, e.g., hydraulic, semi-hydraulic and/or gearing systems. As with instrument 10, a stop is also provided to maintain a minimum gap between the jaw members.

The handle 716 includes handle sections 716a and 716b, and is generally hollow such that a cavity is formed therein for housing various internal components. For example, the cavity can house a PC board which controls the electrosurgical energy being transmitted from the electrosurgical generator 7 to each jaw member, via connector 200. More particularly, electrosurgical energy generated from the electrosurgical generator 7 is transmitted to the handle PC board by a cable 210. The PC board converts the electrosurgical energy from the generator into two different electrical potentials which are transmitted to each jaw member by a separate terminal clip. The handle 716 may also house circuitry that communicates with the generator 7, for example, identifying characteristics of the electrosurgical tool 70 for use by the electrosurgical generator 7, transmitting temperature values, transmitting calculated impedance values, etc.

A lost motion mechanism may be positioned between each of the handle sections 716a and 716b for maintaining a predetermined or maximum clamping force for sealing tissue between the jaw members. It is also contemplated that other endoscopic vessel sealing instruments may be utilized with the present disclosure such as the vessel sealer and dividers, e.g., the LIGASURE ATLAS™ and LIGASURE 5 mm™ manufactured and sold by VALLEYLAB, Inc—a division of TYCO HEALTH CARE GROUP, LP.

Having thus described two exemplary and non-limiting embodiments of surgical instruments 10, 70 that can be employed with the electrosurgical generator 7, a description will now be provided of various aspects of the presently disclosed electrosurgical generator 7.

Figure 8:
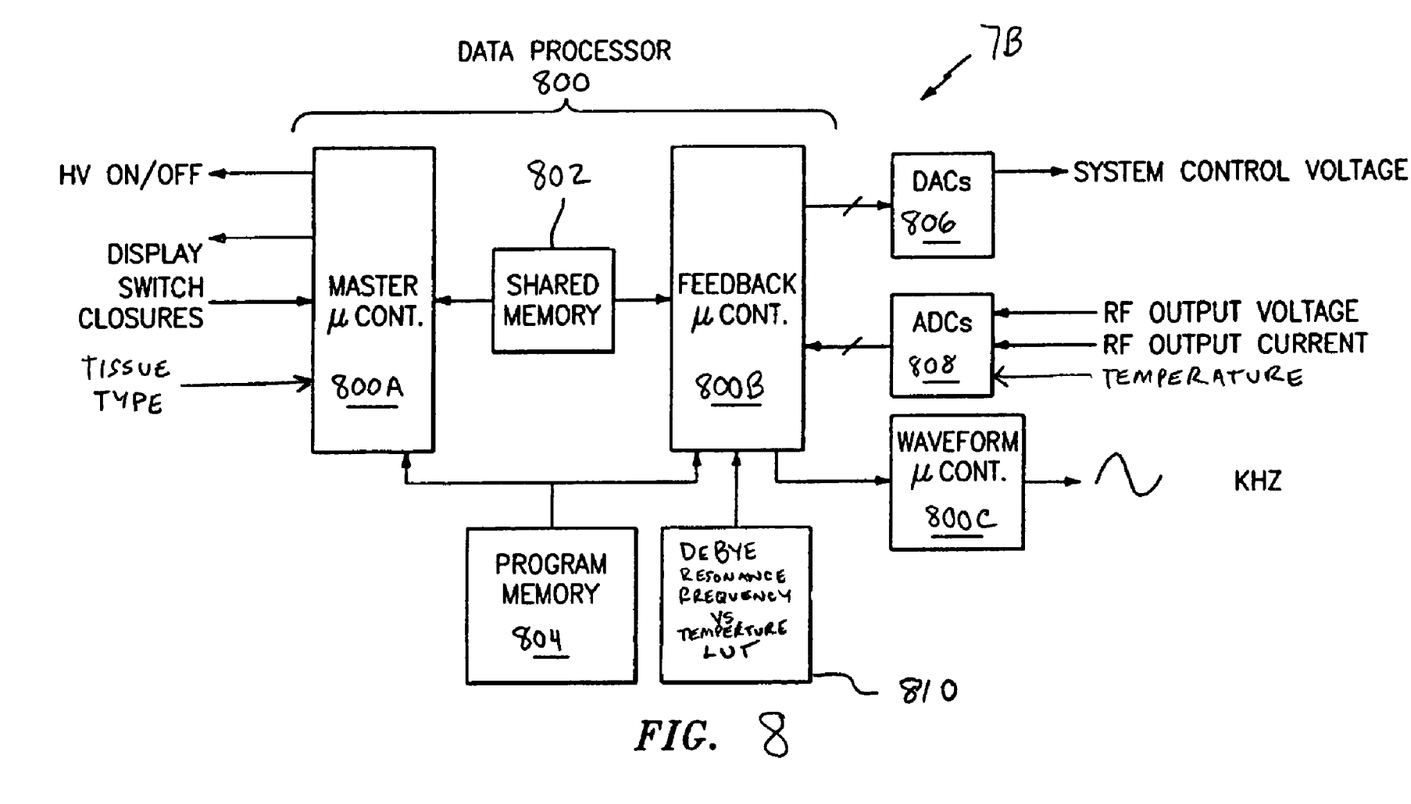
FIG. 8 is a simplified block diagram of one embodiment of a power control circuit for use with an electrosurgical generator.

FIG. 8 is a block diagram that illustrates the power control circuit 7B of FIG. 2 in greater detail. The power control circuit 7B includes a suitably programmed data processor 800 that is preferably implemented as one or more microcontroller devices. In one envisioned embodiment there are two principal microcontrollers, referred to as a main microcontroller 800A and a feedback microcontroller 800B. These two microcontrollers are capable of communicating using shared data that is stored and retrieved from a shared read/write memory 802, e.g., a RAM. A control program for the data processor 800 is stored in a program memory 804, and includes software routines and algorithms for controlling the overall operation of the electrosurgical generator 7. In general, the feedback microcontroller 800B has a digital output bus coupled to an input of a digital to analog converter (DAC) block 806 which outputs an analog signal. This is a system control voltage (SCV), which is applied to the variable DC power supply 7C to control the magnitude of the voltage and current of output RF pulses.

An analog to digital converter (ADC) block 808 receives analog inputs and sources a digital input bus of the feedback microcontroller 800B. Using the ADC block 808, the microcontroller 800B is apprised of the value of the actual output voltage and the actual output current, thereby closing the feedback loop with the SCV signal. The values of the output voltage and current can be used for determining tissue impedance and for the overall, general control of the applied RF energy waveform. It should be noted that at least the ADC block 808 can be an internal block of the feedback microcontroller 800B, and need not be a separate, external component. It should be further noted that the same analog signals can be digitized and read into the master microcontroller 800A, thereby providing redundancy. The master microcontroller 800A controls the state (on/off) of the high voltage (e.g., 190V max) power supply as a safety precaution, controls the front panel display(s), and also receives various input switch closures, such as a tissue type selected by an operator.

It is envisioned that a third (waveform) microcontroller 800C may be employed to generate a desired sinusoidal waveform at a specified Debye resonance frequency that forms the basis of the RF pulses applied to the tissue to be sealed, such as the vessel 400 (FIG. 6). The waveform microcontroller 800C is controlled by the feedback microcontroller 800B and is programmed thereby. Depending on the tissue type, e.g., either selected by the user or sensed via the end effector 100, the feedback controller 800B will access a Debye resonance frequency vs. temperature curve from look-up table (LUT) 810 and will load the appropriate curve from LUT 810. An output signal line from the feedback microcontroller 800B is coupled to an input of the waveform microcontroller 800C to essentially turn the waveform microcontroller 800C on and off to provide the pulsed RF signal in accordance with an aspect of this disclosure. This particular arrangement is, of course, not to be viewed in a limiting sense upon the practice of this system, as those skilled in the art may derive a number of methods and circuits for generating the desired RF pulses in accordance with the teachings found herein.

Furthermore, the ADC 808 will receive a signal indicative of a temperature of the tissue to be sealed and inputs the signal into the feedback microcontroller 800B. The feedback microcontroller 800B will then again access the LUT 810 to determine a shift in the Debye resonance frequency of the tissue selected.

Alternatively, the shift in the Debye resonance frequency of the tissue selected may be determined by a predictive algorithm stored in program memory 804. The predictive algorithm will determine the shift in the Debye resonance frequency from a table derived from experimental data for various tissue types.

Figure 9:
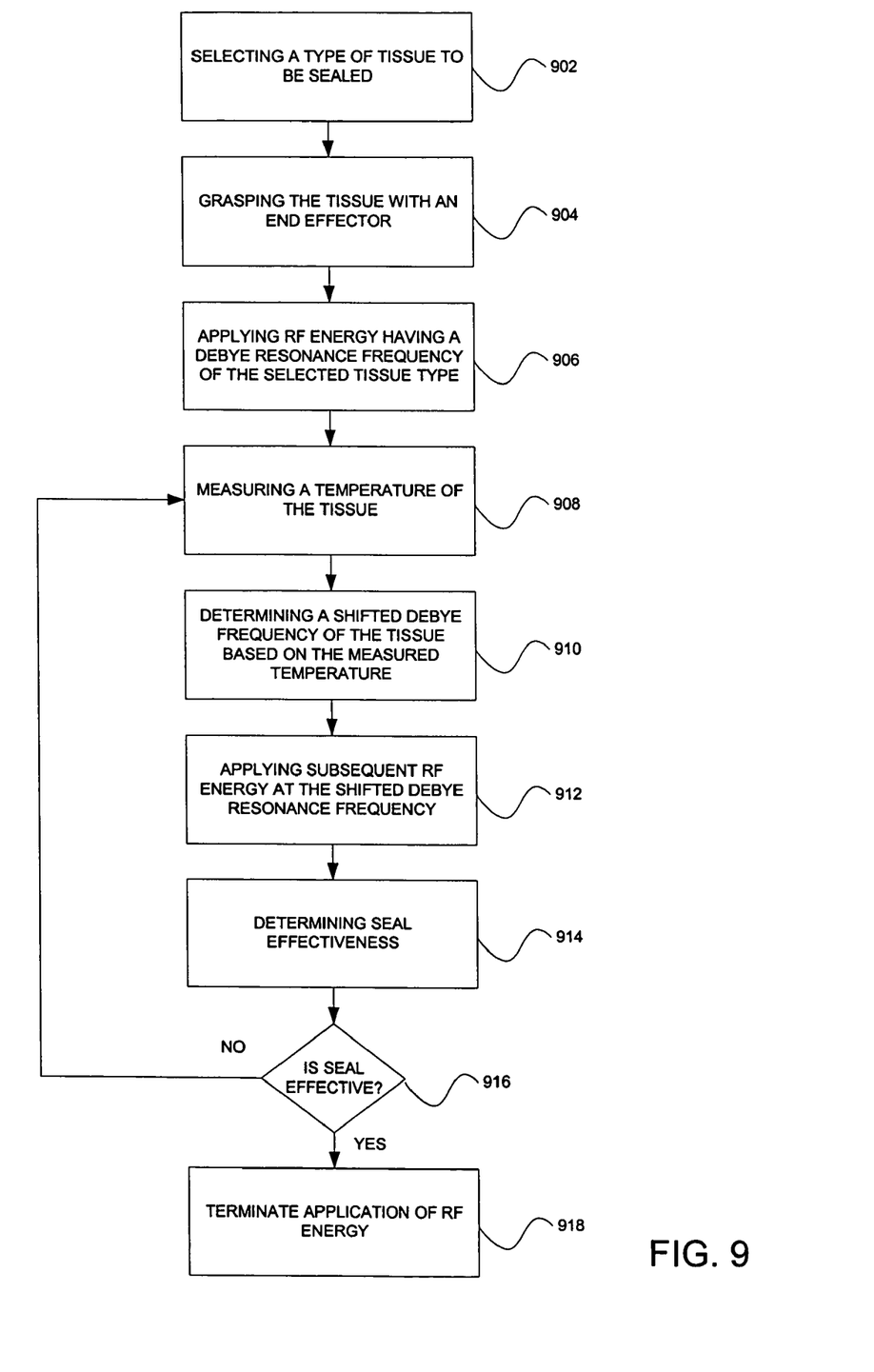
FIG. 9 is a flowchart illustrating one method for sealing tissue according to the present disclosure.

Referring to FIG. 9, a method for electrosurgically sealing tissue using capacitive RF dielectric heating is illustrated. In step 902, a type of tissue to be sealed is determined and selected either manually or automatically by the electrosurgical generator 7. An electrosurgical instrument 10 having an end effector 100 including electrodes having a non-conductive dielectric material disposed thereon is electrically coupled to generator 7 and employed to grasp the tissue to be sealed at the operative site, step 904. The generator will load the appropriate Debye resonance frequency curve based on the type of tissue selected. The generator 7 via waveform generator 800C will apply RF energy at the appropriate Debye resonance frequency to the end effector 100, step 906.

Since the optimal Debye resonance frequency will shift with a change in temperature, temperature sensor 152 will continuously measure the temperature of the tissue to be sealed, in step 908. The temperature will be feedback to the generator 7 via feedback controller 800B and will determine a shifted Debye resonance frequency via the Debye resonance frequency curve for the tissue selected, in step 910. In step 910, the generator 7 will apply subsequent RF energy at the shifted Debye resonance frequency. Alternatively, the shifted Debye resonance frequency will be determined by the predictive algorithm described above.

In step 914, the generator 7 will determine the effectiveness of the seal by determining the impedance of the tissue. The impedance may be determined by sensing the current and voltage of the tissue and calculating the impedance via the appropriate algorithm as is known in the art. In step 916, if the generator 7 determines the seal is effective, the generator will terminate application of the RF energy (step 918) and, optionally, provide an indication to the user that the tissue is sealed. Otherwise, if the seal is not effective, the method will return to step 908 and repeat steps 908 through 916 until it is determines the seal is effective.

It is envisioned that by utilizing a capacitive system for heating, and thus sealing tissue, more uniform heating will be achieved due to the uniform electric field generated between the electrodes of the end effector. Additionally, since the electrodes of the end effector will act as a pure capacitor, there will be no resistive component through the tissue and, therefore, no current which will eliminate the possibility of arcing. Furthermore, since the dielectric material of the end effector will be selected to have superior non-stick properties, the amount of tissue sticking to the end effector will be eliminated or reduced, thus, improving the overall efficacy of the system.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. An electrosurgical instrument for sealing tissue comprising:
   an end effector having opposing jaw members, the jaw members being movable relative to one another from a first position wherein the jaw members are disposed in spaced relation relative to one another to a second position wherein the jaw members cooperate to grasp tissue therebetween, each jaw member including an electrode having a dielectric coating;
   each jaw member adapted to connect to a source of electrosurgical energy to supply electrical energy thereto, the jaw members configured to generate an AC electric field that causes energy to flow through tissue held therebetween at a Debye resonance frequency of the tissue being sealed;
   a control system configured to control the electrical energy supplied to the jaw members based on a sensed strength of the AC electric field; and
   a predictive algorithm executable by the control system and configured to determine a shift in the Debye resonance frequency of the tissue being sealed, the control system adapted to regulate the source of electrical energy to cause energy to flow through the tissue being sealed at the shifted Debye resonance frequency based on the determined shift.

2. The electrosurgical instrument of claim 1, wherein the end effector further comprises at least one temperature sensor for sensing a temperature of the tissue.

3. The electrosurgical instrument of claim 1, wherein the end effector further comprises at least one non-conductive stop member disposed on an inner facing surface of at least one of the jaw members which controls the distance between the jaw members when tissue is held therebetween.

4. The electrosurgical instrument of claim 1, wherein the dielectric coating of the electrodes has a Debye resonance frequency different than the Debye resonance frequency of the tissue.

5. The electrosurgical instrument of claim 1, wherein the dielectric coating is selected from the group consisting of a polyimide film and tetrafluoroethylene.

6. An electrosurgical system comprising:
   an electrosurgical instrument for sealing tissue including an end effector having opposing jaw members, the jaw members being movable relative to one another from a first position wherein the jaw members are disposed in spaced relation relative to one another to a second position wherein the jaw members cooperate to grasp tissue therebetween, each jaw member including an electrode having a dielectric coating;
   an electrosurgical generator coupled to each jaw member and adapted to supply electrosurgical energy thereto, the jaw members configured to generate an AC electric field that causes energy to flow at a predetermined frequency through tissue held therebetween to effect a seal;
   a control system operatively associated with the generator and configured to control the electrosurgical energy supplied to the jaw members based on a sensed strength of the AC electric field; and
   a predictive algorithm executable by the control system and configured to determine a shift in the predetermined frequency of the tissue being sealed, wherein the control system controls the source of electrical energy to cause energy to flow through the tissue being sealed at the shifted predetermined frequency based on the determined shift.

7. The electrosurgical system of claim 6, wherein the end effector further comprises at least one temperature sensor for sensing a temperature of the tissue.

8. The electrosurgical system of claim 6, wherein the end effector further comprises at least one non-conductive stop member disposed on an inner facing surface of at least one of the jaw members which controls the distance between the jaw members when tissue is held therebetween.

9. The electrosurgical system of claim 6, wherein the predetermined frequency is a Debye resonance frequency of the tissue being sealed.

10. The electrosurgical system of claim 9, wherein the dielectric coating of the electrodes has a Debye resonance frequency different than the Debye resonance frequency of the tissue.

11. The electrosurgical system of claim 9, wherein the electrosurgical generator further comprises a look-up table including a plurality of Debye resonance frequencies, each Debye resonance frequency being correlated to a tissue type.

12. The electrosurgical system of claim 9, wherein the electrosurgical generator further comprises a look-up table including a plurality of Debye resonance frequencies versus temperature curves, and the end effector further comprising a temperature sensor for inputting a signal indicative of tissue temperature to the electrosurgical generator, wherein the generator selects an appropriate Debye resonance frequency based on the temperature sensed.

13. The electrosurgical system of claim 6, wherein the dielectric coating is selected from the group consisting of a polyimide film and tetrafluoroethylene.

* * * * *